(12) United States Patent
Pimentel

(10) Patent No.: US 7,534,433 B2
(45) Date of Patent: May 19, 2009

(54) METHOD FOR IMPROVING BODY WEIGHT GAIN AND FEED CONVERSION EFFICIENCY IN ANIMALS

(75) Inventor: Julio Pimentel, Buford, GA (US)

(73) Assignee: Anitox Corporation, Buford, GA (US)

( * ) Notice: Subject to any disclaimer, the term of this patent is extended or adjusted under 35 U.S.C. 154(b) by 174 days.

(21) Appl. No.: 10/163,093

(22) Filed: Jun. 6, 2002

(65) Prior Publication Data

US 2003/0228313 A1 Dec. 11, 2003

(51) Int. Cl.
*A61K 39/395* (2006.01)

(52) U.S. Cl. .............. 424/164.1; 424/130.1; 424/150.1; 424/157.1; 530/387.1; 530/388.26; 530/388.4

(58) Field of Classification Search .............. 424/157.1, 424/130.1; 530/387.1
See application file for complete search history.

(56) References Cited

U.S. PATENT DOCUMENTS

| | | | |
|---|---|---|---|
| 4,863,959 A | | 9/1989 | Bently |
| 4,959,310 A | * | 9/1990 | Brandon et al. ............ 435/7.93 |
| 5,064,655 A | | 11/1991 | Uster |
| 5,080,895 A | * | 1/1992 | Tokoro .................... 424/157.1 |
| 5,741,489 A | * | 4/1998 | Pimentel .................. 424/157.1 |
| 5,827,517 A | | 10/1998 | Cook |
| 5,919,451 A | * | 7/1999 | Cook et al. .............. 424/130.1 |
| 5,976,580 A | | 11/1999 | Ivey |
| 5,985,336 A | | 11/1999 | Ivey |

FOREIGN PATENT DOCUMENTS

DE 0.310.931 12/1989

OTHER PUBLICATIONS

Shipp et al., "Hyperimmune spray dried eggs as a feed supplement for weanling pigs," (1999) Feed Mix, 7:30, 32, 33.*
Carnot et al., 1919, Compt. Rend. 169:88-90 (abstract only).*
(c) 1998, Animal Nutrition Research No. 75, BASF.
Oct. 5-7, 1999, K.F. Cardwell, "Mycotoxin Contamination in Foods—Anti-Nutritional Facts," Improving Human Nutrition Through Agriculture: The Role of Internation Agricultural Research, International Institute of Tropical Agriculute. 08 B.P. 0932. Cotonou Bénin.
2004, I Csaky and S. Fekete, "Soybean: Feed Quality and Safety, Part 1: Biologically Active Components: A Review," Acta Veterinaria Hungarica 52 (3) pp. 299-313.
2004, I Csaky and S. Fekete, "Soybean: Feed Quality and Safety, Part 2: Pathology of Soybean Feeding in Animals: A Review," Acta Veterinaria Hungarica 52 (3) pp. 315-326.
Feb. 2005, Farzana Panhwar, "Anti-nutritonal Factors in Oil Seeds as Aflatoxin in Ground Nuts."
1990, LeClerq et al "Metabolism of VLDL in Genetically Lean or Fat Lines of Chicken," Reproduction, Nutrion, Development 30(6); 705-715.
2005, four pages printed from http://www.fao.org/docrep/R4807E with titles "6. Anti-Nutrional Factors Present in Plant Feedstuff," "7. Adventitious Toxic Factors Present in Foodstuff." and "Anti-nutrional factor".

* cited by examiner

*Primary Examiner*—Michael Szperka
(74) *Attorney, Agent, or Firm*—Neifeld IP Law, PC

(57) ABSTRACT

A method for improving body weight gain and increasing feed conversion efficiency of in animals by feeding the animals a diet containing antibodies against anti-nutritional factors in food.

3 Claims, No Drawings

METHOD FOR IMPROVING BODY WEIGHT GAIN AND FEED CONVERSION EFFICIENCY IN ANIMALS

BACKGROUND OF THE INVENTION

1. Field of the Invention

The invention relates to a method for improving body weight gain and increasing the efficiency of converting feed into body weight gain in animals, by feeding to animals an effective dose of antibodies against anti-nutritional factors commonly found in feedstuffs or produced by microorganisms present in the gastro-intestinal tract.

2. Discussion of the Background

In the animal industry, the feed accounts for 50% to 70% of the overall production cost. Therefore any improvement in the ability of the animal to convert feed into marketable products, e.g., animal body weight, can markedly improve profitability for the animal producer.

Various methods for improving feed conversion are known in the animal industry. One of the most common methods is adding sub-therapeutic levels of antibiotics to the feed, in order to improve animal performance. Antibiotics decrease the animal's exposure to bacterial infection and decrease the number of bacteria in the gastrointestinal tract, thereby allowing the animal to utilize nutrients more efficiently since the animal and the microflora are competing for the same nutrients. However continuous use of antibiotics as growth promoters causes several problems, including the introduction of drug residues in animal produce, promoting the growth of antibiotic resistant bacteria, and increasing the risk of environmental pollution. Due to the seriousness of these problems the use of antibiotics as growth promoters in the animal industry may soon be completely prohibited. The European Union has already banned the use of five different growth promoting antibiotics in animals raised for human consumption and others may follow. In the United States, three growth promoting antibiotics have been banned in recent years.

In order to replace growth-promoting antibiotics several new products have been developed. Enzymes such as phytase, protease and others have been used to assist in the digestion of certain nutrients, improving body weight gain in the animals. This improvement can be attributed to increased digestibility of the nutrients these enzymes help digest rather than to a decrease in gastrointestinal bacteria.

Other methods, such as Competitive Exclusion (CE) and probiotics, have been used to decrease the incidence of pathogenic organisms in animals. In case of CE, the animal is fed a high concentration of "helpful bacteria" that prevent foreign bacteria from colonizing the gastrointestinal tract. Although, CE has been successful in laboratory trials, field results have been inconsistent.

The use of antibodies to prevent certain infections in animals is known to enhance growth performance. Two possible mechanisms by which antibodies prevent infection have been proposed. According to the first mechanism, antibodies decrease the number of foreign bacteria in the gastrointestinal tract by binding to specific receptor sites, thus preventing the foreign bacteria from attaching to the intestine. According to the second mechanism, antibodies may decrease bacterial numbers by binding to specific receptors on the bacteria themselves thus preventing bacterial multiplication.

The effectiveness of avian antibodies in preventing bacterial infections in swine has been reported in several references. In vitro studies reported by Jungling et al. (J. Vet. Med 38:373-381, 1991) suggest that egg yolk antibodies are effective in decreasing the adhesion of enterotoxigenic $E.\ coli$ onto isolated pig enterocytes.

Yokoyama et al. (Infect. Immunity 60:998-1007, 1992 and Am. J. Vet. Res. JY:867-872, 1993) and Erhard et al. (Berl. Munch. Tierarztl. Wschr. 106:383-387, 1993) disclose in vivo tests indicating that spray-dried egg yolk extracts containing antibodies against $E.\ coli$ can prevent colibacillosis in newborn piglets and calves.

Kellner et al. (Jahrgang 49 January 94(1) 31-34, 1994) reported the results of studies demonstrating that spray-dried egg yolk extracts containing antibodies against $E.\ coli$ administered to pigs decreased the number of days that pigs suffered from diarrhea.

U.S. Pat. No. 5,741,489 to Pimentel discloses a method for increasing feed conversion efficiency in pigs and chickens by feeding the animals a diet containing chicken anti-urease antibodies. The reference, however, does not disclose a mixture of antibodies that inhibit several anti-nutritional factors in the animal feed.

The present invention provides an effective and safe method for enhancing body weight gain, feed conversion efficiency or both, in animals, by feeding the animals an antibody against anti-nutritional factors present in the gastrointestinal tract.

SUMMARY OF THE INVENTION

An objective of the present invention is to provide a method for enhancing weight gain and improving feed conversion efficiency, comprising feeding poultry and mammals an effective amount of an antibody against urease, a trypsin inhibitor and/or antibodies against other anti-nutritional factors that are either present in feedstuffs or formed by microorganisms in the gastrointestinal tract of the animal. The invention can be practiced on animals suitable for human consumption, laboratory animals, companion or pet animals and other types of animals. The antibody fed to animals may be present in unfractionated whole egg or egg yolk, and may be freeze dried, spray dried or suspended in a liquid suitable for consumption.

Another objective of the invention is to provide a method of enhancing body weight gain, feed conversion efficiency or both, in animals suffering from body weight loss, by feeding to the animals an effective amount of anti-urease antibodies and antibodies against an anti-nutritional factor during or after the time period when the animal suffers the body weight loss.

DETAILED DESCRIPTION OF THE INVENTION

The present invention comprises feeding animals a diet containing safe and effective amounts of antibodies against anti-nutritional factors. It has been discovered that enhanced weight gain and increased feed conversion efficiency can be achieved by feeding the animals antibodies against anti-nutritional factors found in common feedstuffs or produced by microorganisms normally present in the gastrointestinal tract of the animals.

In the preferred embodiments, animals are fed safe and effective amounts of an antibody against urease together with an antibody against a trypsin inhibitor. Antibodies against urease from Jackbean plant and soybean trypsin inhibitor are preferred. These antibodies are effective at inhibiting the adverse effects of urease and trypsin inhibitors present in the gastrointestinal tract of animals and in feedstuffs. At this time, antibody products fed to animals are anti-bacterial or anti-viral in nature.

Urease in the gastrointestinal tract converts urea to ammonia. When such a reaction occurs the animal must convert the ammonia into non-essential amino acids or the excess ammonia must be detoxified. The detoxification process requires energy, which could better be used for increasing body weight. Urease may also be present in various leguminous plants such as soybean, whether raw soybean or processed soybean meal.

Raw soybean is usually not fed to animals because it contains several anti-nutritional factors including urease and proteases (e.g. a trypsin inhibitor). Trypsin inhibitors inhibit the absorption of proteins by reducing the activity of the enzyme trypsin, which is necessary for degrading proteins to amino acids. Another concern associated with trypsin inhibitors is that they induce the release of cholescystokinin (CCK) which causes satiety and pancreatic hyperplasia.

A heat treatment such as roasting, and other treatments of raw soybean are required to destroy the anti-nutritional factors before feeding it to animals. Soybean meal, the waste product of soybean oil extraction, also requires heat treatment to destroy the anti-nutritional factors. Feeding animals antibodies against urease and trypsin inhibitors improves the performance of animals fed raw soybean or under-processed soybean meal.

By deactivating or decreasing the activity of anti-nutritional factors present in feedstuffs or produced by microorganisms in the gastrointestinal tract, a more efficient process of digestion, absorption and utilization of foods can be achieved.

Antibodies against anti-nutritional factors, such as anti-proteases, gossypol in cottonseed, tannins in sorghum and other anti-nutritional factors present in feedstuffs or formed by microorganisms in the gastrointestinal tract are also within the scope of the present invention and when consumed by the animal improve performance. Suitable anti-proteases include anti-trypsin, anti-chymotrypsin and anti-carboxypeptidase, but the invention is not limited to these three proteases alone, as more may be identified in the future. Antibodies suitable for the present invention are not limited to those against anti-nutritional factors in traditional feedstuffs, and include antibodies for inhibition of detrimental compounds in yucca plants and others. In the preparation of yucca extracts for commercial application, protein cross-linking agents or tanning agents can be formed. These compounds can inactivate gastrointestinal enzymes.

Another embodiment of the invention is directed to a method for enhancing weight gain in animals, especially domesticated companion animals such as cats, dogs, pigs and other companion animals, which may suffer a weight loss due to disease or malnutrition. The method comprises feeding an effective amount of anti-urease antibody to an animal suffering from weight loss after the weight has loss occurred. Alternatively, feeding of anti-urease antibody could be conducted during a period of time when the animal is expected to suffer weight loss, such as during a period of disease known to cause weight loss. The treatment may be continued after the disease is cured until the desired weight gain is achieved.

Non-invasive and inexpensive methods for producing antibodies are known in the art. It has been reported that antibodies specific to Salmonella, E. coli, and other types of bacteria are produced by animals when orally challenged (Ricke et al, Appl. Environ. Microb. 54:596-599, 1988; Neighbor et al, Avian Dis. 35:315-320, 1991).

Another economically feasible method for producing antibodies is injecting hens with antigens. For example, it has been demonstrated that hens injected with a foreign antigen will develop specific antibodies and deposit those antibodies in the egg yolk. It has been observed that eggs contain 50-200 mg of antibodies. When the hen is injected with a particular antigen, 10-20% of the antibody isolated from the egg is specific to that antigen.

Antibodies produced in eggs can be utilized by all animal species. Egg yolk antibodies are absorbed by piglets in a similar manner to homologous pig antibodies. It has been reported that active antibodies were found throughout the distal jejunum in 8 week-old piglets fed lyophilized egg yolk containing antibodies. Also, antibodies have been found to be more resistant to degradation by gastric acidity when they prepared in the form of spray-dried whole egg, as compared to purified spray-dried antibodies.

In the preferred embodiments according to this invention, antibodies against anti-nutritional factors fed to the animals are contained in unfractionated whole eggs, or, preferably, in egg yolk. The whole egg or the egg yolk containing the desired antibodies may be further processed prior to adding them to animal feed. The whole egg or egg yolk can be mixed or diluted with a solvent to form a solution that can be subsequently spray dried or freeze dried. Whole egg or egg yolk solutions containing antibodies can be stored and added to the feed at a later time prior to giving the feed to animals. Liquid eggs can be subject to oxidation and microbial growth. It may be necessary to add an anti-oxidant or preservative. Liquid eggs are usually stored at refrigerated temperatures of 40-50° F. for usually less than a week.

Purified antibodies or antibodies contained in other media fit for animal consumption can also be used in the process according to the invention. Antibodies can be harvested from the colostrum or serum of animals. Antibodies can also be produced in plants, fungi and bacteria through genetic manipulation. These antibodies can be monocolonal or polycolonal.

Estimates of the weight % of antibody in whole egg, egg yolk, dried whole egg, dry egg yolk and suspension concentration with respect to weight of antibody are as follows:

Whole egg (liquid form)—0.2 to 0.6%
Whole egg (dried form)—0.8 to 2.4%
Egg yolk (liquid form)—0.6 to 1.8%
Egg yolk (dried form)—2 to 4%
Suspension concentration depends upon the amount of antibody one wishes to administer to the animal and can range from 0.1 to 99 wt. %, preferably 10 to 50 wt. %.)

The method according to the present invention can be practiced with almost any known wild or domesticated animals, such as animals suitable for human consumption, laboratory animals, and pet or companion animals. Specific examples of animals include bovine, ovine, porcine, chickens, turkeys, ducks, pheasants, pigeons, quails, guinea hens, geese and ratites, dogs, cats, horses and rodents.

The antibodies can be added to any part of the animal diet and can be mixed with solid feedstuff, liquid feedstuff, added to drinking water or fed to animals directly. In the preferred embodiments, the antibodies are mixed with drinking water or solid animal food.

The amounts of antibody added to the feed according to the present invention vary depending on the type of animal and duration of the treatment of animals with antibody. Generally, the antibody is contained in dry whole egg or egg yolk and is added to the animal's diet in an amount from about 1 gram to 50,000 grams per ton of food, preferably 1 to 1,000 grams per ton of food. This refers to spray dried whole egg with an antibody content of 0.8 to 2.4% as described above.

The antibody can be added to drinking water in the form of antibody-containing spray dried whole egg, spray dried egg yolk, freeze dried whole egg, freeze dried egg yolk, whole egg suspension or egg yolk suspension. The amount of the spray dried/freeze dried whole egg suspension typically added to drinking water varies from about 0.5 g to 5,000 g per 1,000 liters of drinking water depending on the type of animals and also on the suspension concentration. For the spray dried or freeze dried whole egg, the range would be 0.004% to 12%.

The diet comprising antibodies against anti-nutritional factors present in feedstuffs or formed by microorganisms in the gastrointestinal tract of said animals can be feed to the animals at any time starting at birth, and can continue for any period of time during the life of the animals. In an animal suitable for human consumption, such as chickens, pigs, etc., it is preferred that antibody feeding be continued from the birth of the animal throughout the lifetime of the animal up to the time of slaughter. The antibody may also be fed to sick or diseased animals until optimum health is obtained.

The invention is further illustrated by the following examples, which are not meant to be limiting.

EXAMPLE 1

Preparation of an Anti-Urease Antibody

Hens were injected with 0.2 mg of urease type II-C (available from Sigma Chemical Company). Inoculum was prepared by dissolving the enzyme in 0.2 ml phosphate buffered saline (PBS; pH 7.3) and 0.2 ml complete Freund's adjuvant. The antigen preparation was injected intramuscularly into two sites, 0.2 ml in each (right and left) pectoral muscle. A total of 0.4 ml of antigen preparation per hen was administered. A second injection was administered 2 weeks following the initial injection. In the second antigen preparation, incomplete Freund's adjuvant was used instead of complete Freund's adjuvant. Hens were re-injected with the antigen preparation every two to four weeks or when the antibody titer was determined to be low. Antibody titer was determined every four weeks by ELISA. Eggs containing the specific antibody were collected 1 week after the second injection.

EXAMPLE 2

The antibody product used for the following animal studies consisted of eggs yolks harvested 21 days after the primary inoculation and dried by spray drying (inlet temperature of 210 F and outlet temperature of 150 F), freeze drying (−60 C. and a vacuum of 60 to 180 millitorr) or diluting to form an aqueous solution (water at a dilution of 1 volume egg yolk and 9 volumes of water.) The harvested yolks were found to contain antibodies against Jackbean urease.

EXAMPLE 3

The first chicken study consisted of a group of one-week-old chicks fed a standard control diet, and a group fed the same diet including a preparation of dried egg yolk containing anti-urease antibodies as described in Example 2. The concentration of antibody in feed was 200 mg of freeze dried whole egg with an antibody concentration of 0.8 to 2.4%. Feed consumption and body weight gains were closely monitored. After one week the feed conversion (grams of feed required to produce one gram in weight gain) for each group was determined. The results are summarized in Table 1:

TABLE 1

| Treatment | Feed intake | Feed conversion |
| --- | --- | --- |
| Control | 420 | 1.50 |
| Anti-urease | 428 | 1.37 |

EXAMPLE 4

The second chicken study consisted of a group of newly hatched chicks fed a standard control diet and a group fed the same diet including a dried egg yolk preparation containing anti-urease antibodies, as described in Example 2, for three weeks. Concentration of antibody in feed was 200 mg of freeze dried whole egg with an antibody concentration of 0.8 to 2.4%. Body weight gain and feed conversion are summarized in Table 2:

TABLE 2

| Treatment | 3-week body weight | 3-week Feed intake | 3-week Feed conversion |
| --- | --- | --- | --- |
| Control | 348 | 672 | 1.93 |
| Anti-urease | 377 | 644 | 1.71 |

The data show that continuous feeding of the antibody results in the best body weight gain and feed conversion.

EXAMPLE 5

This example consisted of two chicken studies done to determine the optimum concentration (mg antibody/kg of feed) required to produce the maximum effect on body weight gain and feed conversion. Three groups of one-day old chickens were fed different levels of antibody extract containing: 0, 32 or 63 mg protein/kg of feed for 4 weeks. Feed consumption and body weight were measured weekly; feed conversion was calculated weekly and expressed as feed intake/body weight gain. The results from the first experiment are summarized in Table 3, and the results from the second experiment are summarized in Table 4.

TABLE 3

| Antibody Concentration | Body weight (g) | | Feed Conversion | |
| --- | --- | --- | --- | --- |
| (mg/kg of feed) | week 3 | Week 4 | Week 3 | Week 4 |
| 0 | 573 | 782 | 1.73 | 1.93 |
| 32 | 614 | 816 | 1.67 | 1.88 |
| 63 | 599 | 790 | 1.68 | 1.89 |

TABLE 4

| Antibody Concentration | Body weight (g) | | Feed Conversion | |
| --- | --- | --- | --- | --- |
| (mg/kg of feed) | week 3 | Week 4 | Week 3 | Week 4 |
| 0 | 550 | 722 | 1.70 | 2.01 |
| 32 | 582 | 743 | 1.62 | 2.00 |
| 63 | 583 | 787 | 1.65 | 1.92 |

EXAMPLE 6

The procedure of Example 5 was followed, except that the chickens were fed differing levels of antibody extract of 0, 25 and 50 mg antibody per kilogram of feed. The results are summarized in Tables 5, 6 and 7.

TABLE 5

| Antibody concentration (mg/kg of feed) | 3-week Body weight | 3-week Feed conversion |
| --- | --- | --- |
| 0 | 567 | 1.70 |
| 50 | 567 | 1.62 |

TABLE 6

| Antibody Concentration | Body weight (g) | | Feed Conversion | |
| --- | --- | --- | --- | --- |
| (mg/kg of feed) | week 3 | week 4 | week 3 | week 4 |
| 0 | 545 | 715 | 1.68 | 1.88 |
| 50 | 565 | 770 | 1.59 | 1.75 |

TABLE 7

| Antibody Concentration | Body weight (g) | | Feed Conversion | |
| --- | --- | --- | --- | --- |
| (mg/kg of feed) | week 3 | week 4 | week 3 | week 4 |
| 0 | 494 | 741 | 1.85 | 2.01 |
| 25 | 506 | 730 | 1.78 | 1.95 |
| 50 | 522 | 763 | 1.77 | 1.91 |

Conclusion: There is a optimally effective dose of the antibody. As the concentration of the antibody fed to the animal increases the improvements in body weight gain and feed conversion also increase. The optimum concentration is obtained when higher levels do not result in any additional improvements in performance.

It will be apparent for those skilled in the art that a number of modifications and variations may be made without departing from the scope of the present invention as set forth in the claims.

REFERENCES

1. Bartz, C. R., R. H. Conklin, C. B. Tunstall and J. H. Steele (1980). Prevention of murine rotavirus infection with chicken egg yolk immunoglobulins. J. Infect. Dis. 142: 439-441.
2. Burdsall, H. H., M. Banik, M. E. Cook (1990). Serological differentiation of three species of Armillaria and Lentinula by enzyme-linked immunosorbent assay using immunized chickens as a source of antibodies. Mycologia 84: 415-423.
3. Cook M. E., C. C. Miller and J. L. Pimentel (1998). CCK antibodies used to improved feed efficiency U.S. Pat. No. 5,827,517.
4. Cook M. E., C. C. Miller and J. L. Pimentel (1998). Novel compound to mimic a naturally occurring peptide's effect. U.S. Pat. No. 5,814,316.
5. Cook M. E., C. C. Miller and J. L. Pimentel (1999). CCK antibodies used to improved feed efficiency, U.S. Pat. No. 5,989,584.
6. Erhard, M. H., J. Kellner, J. Eichelberger and U. Losch (1993). New aspects in oral immunoprophylaxis for the prevention of infectious diarrhea of newborn calves—a field study with specific egg antibodies. Berl. Munch. Tierarztl. Wschr. 106:383-387.
7. Gassmann, M., P. Thommes, T. Weiser and U. Hubscher (1990). Efficient production of chicken egg antibodies against a conserved mammalian protein. Faseb J. 4:2528-2532.
8. Hatta, H; K. Tsuda, S. Akachi, M. Kim and T. Yamamoto (1993a). Productivity and some properties of egg yolk antibody (IgY) against human rotavirus compared with rabbit IgG. Biosci. Biotech. Biochem. 57:450-454.
9. Hatta, H., K. Tsuda, S. Akachi, M. Kim, T. Yamamoto and T. Ebina (1993b). Oral passive immunization effect of anti-human rotavirus IgY and its behavior against proteolytic enzymes. Biosci. Biotech. Biochem. 57:1077-1081.
10. Ishida, A, Y. Yoshikai, S. Murosaki, C. Kubo, Y. Hidaka, and K. Nomoto (1992). Consumption of milk from cows immunized with intestinal bacteria influences age-related changes in immune competence in mice. J. Nutrition 122: 1875-1883.
11. Jungling, A., V. Wiedemann, R. Kuhlmann, M. Erhard, P. Schmidt and U. Losch (1991). Chicken egg antibodies for prophylaxis and therapy of infectious intestinal diseases. J. Vet. Med 38:373-381.
12. Kellner, J. M. H. Erhard, M. Renner and U Losch (1993). a field trial of the treatment of diarrhea in piglets with specific egg antibodies. Jahrgang (49) January 94(1) 31-34.
13. Kuhlmann, R., V. Wiedemann, P. Schmidt, R. Wanke, E. Linckh and U. Losch (1988). Chicken egg antibodies for prophylaxis and therapy of infectious intestinal diseases. I.—Immunization and antibody determination. J. Vet. Med. B. 35:610-616.
14. Kuroki, M., Y. Ikemori, H. Yokoyama, R. Peralta, F. Icatlo and Y. Kodama (1993). Passive protection against bovine rotavirus-induced diarrhea in murine model by specific immunoglobulins from chicken egg yolk. Vet. Micro. 37:135-146.
15. Losch, U., I. Strainer, R. Wanke and L. Jargons (1986). The chicken egg, an antibody source. J. Vet. Med. B. 33:609-619.
16. Neighbor, N. K., J. K. Skeeles, J. N. Beasley and D. L. Kreider (1991). Use of an enzyme-linked immunosorbent assay to measure antibody levels in turkey breeders hens, eggs, and progeny following natural infection or immunization with a commercial Bordetella avium bacterin. Avian Dis. 35:315-320.
17. Pimentel J. L. (1998). Passively administered antibody that enhanced feed conversion efficiency U.S. Pat. No. 5,741,489.
18. Ricke, S. C., D. M. Schaefer and M. E. Cook (1988). Differentiation of ruminal bacterial species by enzyme-linked immunosorbent assay using egg yolk antibodies from immunized hens. Appl. Environ. Microb. 54:596-599.
19. Schmidt, P. ,V. Wiedemann, R. Kuhlmann, R. Wanke, E. Linckh and U. Losch (1989). Chicken egg antibodies for prophylaxis and therapy of infectious diseases. II.—In vitro studies on gastric and enteric digestion of egg yolk antibodies specific against pathogenic *Escherichia coli* strains. J. Vet. Med. B. 36:619-628.
20. Sherman, D. M., S. D. Acres, P. L. Sadowski, J. A. Springer, B. Bau, T. J. G. Raybould and C. C. Muscoplat (1983). Protection of calves against fatal enteric colibacillosis by orally administered *Escherichia coli* K99-specific monoclonal antibody. Infect. Immun. 42:653-658.
21. Wiedemann, V., R. Kuhlmann, P. Schmidt, W. Erhardt and U. Losch (1990). Chicken egg antibodies for prophylaxis and therapy of infectious intestinal diseases. III.—In vivo tenacity test in piglets with artificial jejunal fistula. J. Vet. Med. B. 37:163-172.
22. Yokoyama, H., R. Peralta, R. Diaz, S. Sendo, Y. Ikemori and Y. Kodana (1992). Passive protective effect of chicken egg yolk immunoglobulins against experimental enterotoxigenic *Escherichia coli* infection in neonatal piglets. Infect. Immunity 60:998-1007.
23. Yokoyann, H., R. Peralta, S. Serdo, Y. Ikemori (1993). Detection of passage and absorption of chicken egg yolk immunoglobulins in the gastrointestinal tract of pigs by the use of enzyme-linked immunosorbent assay and fluorescent antibody testing. Am. J. Vet. Res. JY:867-872.
24. Yolker, R. H., F. Leister, S. B. Wee, R. Miskuff and V. Vonderfecth (1988) Antibodies to rotaviruses in chicken's eggs: a potential source of antiviral immunoglobulin suitable for human consumption. Pediatrics 81:291-295.

The invention claimed is:

1. A method for enhancing body weight gain or feed conversion efficiency in chickens, comprising: feeding chickens an effective amount of a composition containing a first antibody against urease and a second antibody against a trypsin inhibitor.

2. The method of claim 1 further comprising feeding said animal raw soybean product.

3. The method of claim 1 further comprising spray spray or freeze drying said first antibody and said second antibody.

* * * * *